(12) United States Patent
Pak

(10) Patent No.: US 9,096,563 B2
(45) Date of Patent: Aug. 4, 2015

(54) START-UP PROCESS FOR HIGH SELECTIVITY ETHYLENE OXIDE CATALYSTS

(71) Applicant: Scientific Design Company, Inc., Little Ferry, NJ (US)

(72) Inventor: Serguei Pak, Teaneck, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 14/144,752

(22) Filed: Dec. 31, 2013

(65) Prior Publication Data

US 2014/0187807 A1    Jul. 3, 2014

Related U.S. Application Data

(60) Provisional application No. 61/747,521, filed on Dec. 31, 2012.

(51) Int. Cl.
*C07D 301/10* (2006.01)
*C07D 301/03* (2006.01)

(52) U.S. Cl.
CPC .................. *C07D 301/10* (2013.01)

(58) Field of Classification Search
CPC ........................ C07D 301/10; C07D 301/03
USPC ................................... 549/536, 534
See application file for complete search history.

(56) References Cited

U.S. PATENT DOCUMENTS

| | | |
|---|---|---|
| 3,563,914 A | 2/1971 | Wattmena |
| 3,702,259 A | 11/1972 | Neilsen |
| 4,761,394 A | 8/1988 | Lauritzen |
| 4,766,105 A | 8/1988 | Lauritzen |
| 4,874,879 A | 10/1989 | Lauritzen et al. |
| 4,908,343 A | 3/1990 | Bhasin |
| 5,011,807 A | 4/1991 | Hayden et al. |
| 5,057,481 A | 10/1991 | Bhasin |
| 5,099,041 A | 3/1992 | Hayden et al. |
| 5,102,848 A | 4/1992 | Soo et al. |
| 5,112,795 A | 5/1992 | Minahan et al. |
| 5,155,242 A | 10/1992 | Shankar et al. |
| 5,187,140 A | 2/1993 | Thorsteinson et al. |
| 5,407,888 A | 4/1995 | Herzog et al. |
| 7,102,022 B2 | 9/2006 | Evans et al. |
| 7,553,980 B2 | 6/2009 | Rizkalla et al. |
| 2004/0049061 A1 | 3/2004 | Lockemeyer et al. |
| 2008/0015393 A1 | 1/2008 | Matusz et al. |
| 2009/0281339 A1 | 11/2009 | Matusz et al. |
| 2011/0152073 A1 | 6/2011 | Dialer et al. |
| 2011/0152548 A1 | 6/2011 | Sachs et al. |
| 2011/0152549 A1 | 6/2011 | Rizkalla et al. |

FOREIGN PATENT DOCUMENTS

WO    WO2004002972    1/2004

OTHER PUBLICATIONS

Drake, L.C., et al., "Macropore-Size Distributions in Some Typical Porous Substances", Ind. Eng. Chem. Anal. Ed., Publication Date: Dec. 1945 (12), pp. 787-791.
Brunauer, S., et al., "Adsorption of Gases in Multimolecular Layers", J. Am. Chem. Soc., Feb. 1938, pp. 309-316.
International Search Report dated Apr. 14, 2014, received in a corresponding foreign application.

*Primary Examiner* — T. Victor Oh
(74) *Attorney, Agent, or Firm* — Scully, Scott, Murphy & Presser, P.C.

(57) ABSTRACT

A high selectivity catalyst start-up process is provided in which an excess level of chloride moderator (greater than 1 ppm) is present in the feed gas composition during each of the various stages of the start-up process. The excess level of chloride used in the start-up process maintains a low level of selectivity (less than 86%) during the entire start-up process. Despite the low selectivity values achieved during the start-up process of the present disclosure, high selectivity catalysts that are conditioned by such a start-up process exhibit improved catalyst performance during the normal operation of the catalyst.

16 Claims, No Drawings

START-UP PROCESS FOR HIGH SELECTIVITY ETHYLENE OXIDE CATALYSTS

CROSS REFERENCE TO RELATED APPLICATION

The present invention claims the benefit of U.S. Provisional Patent Application No. 61/747,521 filed Dec. 31, 2012, the entire content and disclosure of which is incorporated herein by reference.

FIELD OF THE DISCLOSURE

The present disclosure relates to the production of ethylene oxide using a high selectivity silver (Ag)-based catalyst. More particularly, the present disclosure relates to a start-up process that can be used to initiate a high selectivity Ag-based catalyst.

BACKGROUND

Though present in natural settings at minute quantities, ethylene oxide was first synthesized in a laboratory setting in 1859 by French chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by another French chemist Theodore Lefort. Lefort used a solid silver catalyst with a gas phase feed that included ethylene and utilized air as a source of oxygen.

In the eighty years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation. About two thirds of the ethylene oxide produced is further processed into ethylene glycol, while about ten percent of manufactured ethylene oxide is used directly in applications such as vapor sterilization.

The growth in the production of ethylene oxide has been accompanied by continued intensive research on ethylene oxide catalysis and processing, which remains a subject of fascination for researchers in both industry and academia. Of particular interest in recent years has been the proper operating and processing parameters for the production of ethylene oxide using so-called "high selectivity catalysts", i.e., a catalyst that possess selectivity values higher than high activity catalysts (HACs) used for the same purpose. Both types of catalysts include silver as the active catalytic component on a refractory support (i.e., carrier). Typically, one or more promoters are included in the catalyst to improve or adjust properties of the catalyst, such as selectivity.

Generally, but not necessarily always, HSCs achieve the higher selectivity (typically, in excess of 87 mole % or above) by incorporation of rhenium as a promoter. Typically, one or more additional promoters selected from alkali metals (e.g., cesium), alkaline earth metals, transition metals (e.g., tungsten compounds), and main group non-metals (e.g., sulfur and/or halide compounds) are also included. There are also ethylene epoxidation catalysts that may not possess the selectivity values typically associated with HSCs, though the selectivity values are improved over HACs. These types of catalysts can also be considered within the class of HSCs, or alternatively, they can be considered to belong to a separate class, e.g., "medium selectivity catalysts" or "MSCs." These types of catalysts typically exhibit selectivities of at least 83 mole % and up to 87 mole %.

In contrast to HSCs and MSCs, the HACs are ethylene epoxidation catalysts that generally do not include rhenium (Re), and for this reason, do not provide the selectivity values of HSCs or MSCs. Typically, HACs include cesium (Cs) as the main promoter.

With respect to these Re-containing Ag-based catalysts there has been considerable interest in determining the optimum start-up (also commonly referred to as "initiation" or "activation") conditions, since Re-containing Ag-based catalysts require an initiation period to maximize selectivity.

Initiation procedures were previously disclosed in U.S. Pat. No. 4,874,879 to Lauritzen et al. and U.S. Pat. No. 5,155, 242 to Shanker et al., which disclose start-up processes in which Re-containing catalysts are pre-chlorinated prior to the introduction of oxygen into the feed and the catalysts are allowed to "pre-soak" in the presence of the chloride at a temperature below that of the operating temperature. While some improvement in overall catalyst performance has been reported using these methods, the pre-soaking and conditioning nonetheless impose a substantial delay before normal ethylene oxide production can begin after oxygen is added into the feed. This delay in production may either partially or entirely negate the benefit of increased selectivity performance of the catalyst. Additionally, in order to reduce the deleterious effects on catalyst performance caused by overchloriding during the pre-soak phase, it is often necessary to conduct an additional chlorine removal step where the ethylene (or some other suitable hydrocarbon such as ethane) is used at elevated temperatures to remove some of the chloride from the surface of the catalyst.

More recently it has been proposed to contact a Re-containing catalyst bed with a feed comprising oxygen and holding the temperature of the catalyst bed at high temperatures for several hours as part of the conditioning process. Again, while some improvement in catalyst performance may be obtained by this method, there are also inherent disadvantages to this process, notably the high temperatures required during start-up.

Despite the above start-up processes, and because of the importance for operating high selectivity Ag-based catalysts under optimum conditions, there is a continued need to develop new and improved start-up operations that can be used to initiate the gas phase epoxidation of ethylene to ethylene oxide using such catalysts.

SUMMARY

A high selectivity catalyst start-up (also commonly referred to as "initiation" or "activation") process is provided in which an excess level of chloride moderator (greater than 1 ppm) is present in the feed gas composition during each of the various stages of the start-up process. The excess level of chloride used in the start-up process maintains a low level of selectivity (less than 86%) during the entire start-up process.

Despite the low selectivity values achieved during the start-up process of the present disclosure, high selectivity catalysts that are conditioned by the start-up process of the present disclosure exhibit improved catalyst performance during the normal operation of the catalyst.

In one aspect of the present disclosure, a start-up process is provided. The start-up process of the present disclosure includes initiating an epoxidation reaction by reacting a feed gas composition containing ethylene, oxygen and a chloride moderator in the presence of a silver-based epoxidation catalyst at a first temperature from about 180° C. to about 230° C., wherein said chloride moderator is present in the feed gas composition at a concentration of greater than 1 ppm, and wherein said epoxidation reaction has a selectivity of less than 86%; increasing the first temperature to a second temperature of about 235° C. to about 270° C. at a ramp of 0.5° C./h to about 10° C./h in the presence of the feed gas composition used during said initiating; maintaining the second temperature over a time period of from about 10 hours to about 400 hours in the presence of the feed gas composition used during said initiating; reducing the concentration of the chloride moderator in the feed gas composition below that used during said initiating; and reducing the second temperature to a third temperature in the presence of said feed gas composition including said reduced concentration of chloride moderator.

DETAILED DESCRIPTION

Before further describing the start-up process of the present disclosure, a description of the high selectivity catalyst that can be employed in the present disclosure is now provided. The high selectivity catalyst employed in the present disclosure is any silver-based catalyst which achieves a selectivity that is greater than 83 mole %, more typically greater than 87 mole %.

The carrier, i.e., support, which can be employed in this disclosure may be selected from a large number of solid, refractory carriers that may be porous. The carrier may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. In one embodiment of the present disclosure, the carrier that can be used in the present disclosure comprises an alpha-alumina carrier having a very high purity; i.e., at least 90 wt. % pure, more preferably, at least 95 wt. % and even more preferably at least 98 wt. % alpha-alumina. In yet another embodiment, the carrier may comprise alpha-alumina having a purity from 80 wt. % to 90 wt. %. The remaining components of the alpha-alumina carrier may include inorganic oxides other than alpha-alumina, such as silica, alkali metal oxides (e.g., sodium oxide) and trace amounts of other metal-containing or non-metal-containing additives or impurities.

The carrier may be made utilizing conventional techniques well known to those skilled in the art. Alternatively, the carrier may be purchased from a catalyst carrier provider.

In one embodiment, the carrier is porous and has a B.E.T. surface area of at most 20 m$^2$/g. In another embodiment, the carrier is porous and has a B.E.T. surface area from 0.1 m$^2$/g to 10 m$^2$/g. In yet another embodiment, the carrier is porous and has a B.E.T. surface area from 0.5 m$^2$/g to 5 m$^2$/g. As used herein, the B.E.T. surface area is deemed to have been measured by the method as described in Brunauer, Emmet and Teller in J. Am. Chem. Soc, 60 (1938) 309-316.

The carrier typically possesses a water absorption value ranging from about 0.2 cc/g to about 0.8 cc/g, and more typically from about 0.25 cc/g to about 0.6 cc/g.

The carrier can have any suitable distribution of pore diameters. As used herein, the "pore diameter" is used interchangeably with "pore size". Typically, the pore diameters are at least about 0.01 microns (0.01 µm), and more typically, at least about 0.1 µm. In different embodiments, the pore diameters can be at least about 0.2 µm, or 0.3 µm. Typically, the pore diameters are no more than about 50 µm.

The carrier of the present disclosure can be monomodal or multimodal such as, for example, bimodal. Without wishing to be bound by any theory, it is believed that a catalyst with a bimodal pore size distribution possesses a type of pore structure in which reaction chambers are separated by diffusion channels.

In one embodiment, at least 40% (and typically at least 60%, and more typically at least 80%) of the pore volume is due to pores with diameters between 1 and 5 micrometers. The median pore diameter of the carrier employed is typically between about 1 and 5 micrometers, more typically between about 1 and 4.5 micrometers, and even more typically between about 1 and 4 micrometers. The pore volume from pores with a diameter of 5 micrometers and above is typically less than about 0.20 ml/g, more typically less than about 0.10 ml/g, and even more typically less than about 0.05 ml/g. The pore volume from pores with a diameter of 1 micrometer and less is typically less than about 0.20 ml/g, more typically less than about 0.16 ml/g.

In some embodiments, the water pore volume can be from about 0.10 cc/g to about 0.80 cc/g, and more typically from about 0.20 cc/g to about 0.60 cc/g. The pore volume and pore size distribution described herein can be measured by any suitable method, but are more preferably obtained by the conventional mercury porosimeter method as described in, for example, Drake and Ritter, "Ind. Eng. Chem. Anal. Ed.," 17, 787 (1945).

Regardless of the character of the carrier used, it is usually shaped into particles, chunks, pieces, pellets, rings, spheres, wagon wheels, cross-partitioned hollow cylinders, and the like, of a size suitable for employment in fixed-bed epoxidation reactors. Desirably, the carrier particles may have equivalent diameters which are typically in the range from about 3 mm to about 12 mm and more typically in the range from about 5 mm to about 10 mm, which are usually compatible with the internal diameter of the tubular reactors in which the catalyst is placed. Equivalent diameter is the diameter of a sphere having the same external surface (i.e., neglecting surface within the pores of the particle) to volume ratio as the carrier particles being employed.

In order to produce a catalyst for the oxidation of ethylene to ethylene oxide, a carrier having the above characteristics is then provided with a catalytically effective amount of silver on its surface. The catalyst is prepared by impregnating the carrier with a silver compound, complex or salt dissolved in a suitable solvent. In one embodiment, an aqueous silver solution is used. After impregnation, the excess solution is removed from the impregnated carrier, and the impregnated carrier is heated to evaporate the solvent and to deposit the silver or silver compound on the carrier as is known in the art.

In some embodiments of the present disclosure, the catalysts prepared contain up to about 45% by weight of silver, expressed as metal, based on the total weight of the catalyst including the carrier. The silver is deposited upon the surface and throughout the pores of a porous refractory carrier. In some embodiments, silver contents, expressed as metal from about 1% to about 40% based on the total weight of the catalyst can be employed. In another embodiment, the silver contents from about 8% to about 35% can be employed. The amount of silver deposited on the carrier or present on the carrier is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide. Useful silver containing compounds which are silver precursors non-exclusively include silver nitrate, silver oxide, or a silver carboxylate, e.g., silver oxalate, silver citrate, silver phthalate, silver lactate, silver propionate, silver butyrate and higher fatty acid salts and combinations thereof.

Also deposited on the carrier, either prior to, coincidentally with, or subsequent to the deposition of the silver is a promoting amount of a rhenium component, which may be a rhenium-containing compound or a rhenium-containing complex. In one embodiment, the rhenium promoter may be present in an amount from about 0.001 wt. % to about 1 wt. % based on the weight of the total catalyst including the carrier, expressed as the rhenium metal. In another embodiment, the rhenium promoter may be present in an amount from about 0.005 wt. % to about 0.5 wt. % based on the weight of the total catalyst including the carrier. In yet a further embodiment, the rhenium promoter may be present in an amount from about 0.01 wt. % to about 0.1 wt. % based on the weight of the total catalyst including the carrier.

Also deposited on the carrier either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The carrier may be impregnated at the same time or in separate steps with the various catalyst promoters. The particular combination of silver, carrier, alkali metal promoters, rhenium component, and optional additional promoters of the instant disclosure will provide an improvement in one or more catalytic properties over the same combination of silver and carrier and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the carrier, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity. In the epoxidation process, it may be desirable to intentionally change the operating conditions to take advantage of certain catalytic properties even at the expense of other catalytic properties. The exact operating conditions will depend upon, among other factors, feedstock costs, energy costs, by-product removal costs and the like.

Suitable alkali metal promoters may be selected from lithium, sodium, potassium, rubidium, cesium or combinations thereof. In one embodiment, the alkali metal promoter includes cesium. In another embodiment, the alkali metal promoter includes combinations of cesium with other alkali metals such as, for example, lithium. The amount of alkali metal deposited or present on the carrier is to be a promoting amount. In one embodiment, the alkali metal promoters are present in an amount that ranges from about 10 ppm to about 3000 ppm by weight of the total catalyst, measured as the metal. In another embodiment, the alkali metal promoters are present in an amount that ranges from about 15 ppm to about 2000 ppm by weight of the total catalyst, measured as the metal. In a further embodiment, the alkali metal promoters are present in an amount that ranges from about 20 ppm to about 1500 ppm by weight of the total catalyst, measured as the metal. In a yet further embodiment, the alkali metal promoters are present in an amount that ranges from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. In one embodiment, the transition metal comprises an element selected from Groups IVA, VA or VIA of the Periodic Table of the Elements. In a further embodiment, the transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the carrier is a promoting amount. In one embodiment, the transition metal promoter is present in an amount from about 10 parts per million to about 1000 parts per million of total catalyst expressed as the metal. In another embodiment, the transition metal promoter is present in an amount from about 20 parts per million to about 500 parts per million of total catalyst expressed as the metal. In a further embodiment, the transition metal promoter is present in an amount from about 30 parts per million to about 350 parts per million of total catalyst expressed as the metal. The catalyst may further comprise a promoting amount of one or more sulfur compounds, one or more phosphorus compounds, one or more boron compounds, one or more halogen-containing compounds, or combinations thereof.

The silver solution used to impregnate the carrier may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include a diamino alkane having from 1 to 5 carbon atoms. In one embodiment, the solution comprises an aqueous solution of silver oxalate and ethylene diamine. The complexing/solubilizing agent may be present in the impregnating solution in an amount from about 0.1 to about 5.0 moles per each mole of silver. In another embodiment, the complexing/solubilizing agent may be present in the impregnating solution in an amount from about 0.2 to about 4.0 moles per each mole of silver. In yet another embodiment, the complexing/solubilizing agent may be present in the impregnating solution in an amount from about 0.3 to about 3.0 moles per each mole of silver. When a solvent is used, it may be an organic solvent or water, and may be polar or substantially non-polar. In general, the solvent should have sufficient solvating power to solubilize the solution components. At the same time, it is preferred that the solvent be chosen to avoid having an undue influence on, or interaction with, the solvated promoters.

The concentration of silver in the impregnating solution is typically in the range from about 1.0% by weight up to the maximum solubility afforded by the particular solvent/solubilizing agent combination employed. It is generally very suitable to employ solutions containing from about 5% to about 45% by weight of silver. In some embodiments, the solutions contains from about 10 to about 35% by weight of silver.

Impregnation of the selected carrier is achieved using any of the conventional methods; for example, excess solution impregnation, incipient wetness impregnation, spray coating, etc. Typically, the carrier material is placed in contact with the silver-containing solution until a sufficient amount of the solution is absorbed by the carrier. A single impregnation or a series of impregnations, with or without intermediate drying, may be used, depending, in part, on the concentration of the silver component in the solution. Impregnation procedures are described in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the carrier with the silver-containing compound, i.e., a silver precursor, rhenium component, and other desired promoters, the impregnated carrier is calcined for a time sufficient to convert the silver containing compound to metallic silver and to remove the volatile components from the impregnated carrier to result in a catalyst precursor. In one embodiment, the calcination may be accomplished by heating the impregnated carrier, preferably at a gradual rate, to a temperature in the range from about 200° C. to about 600° C. In another embodiment, the calcination can be performed at a temperature from about 200° C. to about 500° C. In yet another embodiment, the calcination can be performed at a temperature from about 200° C. to about 450° C. The calcination is typically performed at a pressure in the range from 0.5 bar to 35 bar. In general, the higher the temperature, the shorter the required heating period. A wide range of heating periods have been suggested in the art; e.g., U.S. Pat. No. 3,563,914 suggests heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver compound is converted to metallic silver. Continuous or step-wise heating may be used for this purpose.

During calcination, the impregnated carrier may be exposed to a gas atmosphere comprising an inert gas or a mixture of an inert gas with from about 10 ppm to about 21% by volume of oxygen.

After calcining the high selectivity catalyst, the calcined catalyst is loaded into reactor tubes of an epoxidation reactor, typically a fixed bed, tubular reactor, utilizing conventional loading methods well known to those skilled in the art. After loading, the catalyst bed may be swept by passing an inert gas such as nitrogen over the catalyst bed. This sweeping process is typically performed at a temperature from about 100° C. to about 230° C. for a time period from 0.5 hours to 100 hours.

After performing the sweeping process, the high selectivity catalyst is subjected to the start-up process of the present disclosure. In some embodiments of the present disclosure and prior to performing the start-up process, the high selectively catalyst can be treated in a gas stream containing a chloride moderator; no other gases such as ethylene and/or oxygen are present during this treatment process. When such a treatment is performed, the treatment can be carried out within a temperature range from 100° C. to 300° C. In another embodiment, this treatment can be performed within a temperature range from 150° to 290° C. In yet another embodiment, this treatment can be performed within a temperature range from 200° C. to 280° C. Notwithstanding the temperature of this treatment, the treatment can be performed for a duration of time from about 0.5 hours to about 200 hours. In one embodiment, the concentration of chloride moderator used in this treatment process is greater than 1 ppm. In another embodiment, the concentration of chloride moderator used during the treatment process is greater than 2 ppm. In yet another embodiment, the concentration of chloride moderator used during the treatment process is greater than 4 ppm.

The chloride moderators which can be employed in the present disclosure include, but are not limited to, organic halides such as $C_1$ to $C_8$ halohydrocarbons; such, as for example, methyl chloride, ethyl chloride, ethylene dichloride, vinyl chloride or mixtures thereof. Also suitable are hydrogen-free chlorine sources such as perhalogenated hydrocarbons and diatomic chlorine are particularly effective as moderators in gas phase epoxidation. Perhalogenated hydrocarbons refer to organic molecules in which all of the hydrogen atoms in a hydrocarbon have been substituted with halogen atoms; suitable examples are trichlorofluormethane and perchloroethylene.

In the start-up process of the present disclosure, the high selectivity catalyst (which may or may not be subjected to the treatment process described above) is heated to a first temperature of about 180° C. to about 230° C., which is sufficient to initiate an epoxidation reaction, while pressurizing a recycle loop of the epoxidation reactor with a feed gas composition including ethylene, oxygen, a chloride moderator and a suitable ballast gas such as methane or nitrogen. Typically, nitrogen is used as the ballast gas.

In one embodiment, the concentration of oxygen that is present in the feed gas composition during this initiation stage is from about 0.3 volume % to about 7 volume %.

In one embodiment, the concentration of ethylene that is present in the feed gas composition during this initiation stage is from about 3 volume % to about 30 volume %.

An excess concentration of chloride moderator is present in the feed gas composition during this initiation stage of the start-up process. By "excess level" is meant that the chloride moderator is present in a sufficient concentration which will maintain a selectivity value of the epoxidation reaction below 86%, more typically below 83%, and even more typically below 80%. In one embodiment of the present disclosure, the concentration of chloride moderator that is present in the feed gas composition during the initiation stage of the start-up process is greater than 1 ppm. In another embodiment, the concentration of chloride moderator that is present in the feed gas composition during the initiation stage of the start-up process is greater than 2 ppm. In a yet further embodiment of the present disclosure, the concentration of chloride moderator that is present in the feed gas composition during the initiation stage of the start-up process is greater than 4 ppm.

After the epoxidation reaction is initiated as described above and as the reaction continues, the temperature is increased from the first temperature to a second temperature which is greater than the first temperature. In one embodiment, the second temperature is from about 235° C. to about 270° C. In another embodiment, the second temperature is from about 240° C. to about 265° C. In yet another embodiment, the second temperature is from about 245° C. to about 260° C. The temperature is increased from the first temperature to the second temperature typically at a rate of 0.5° C./h to about 10° C./h. As the temperature is increased the levels of oxygen, ethylene and chloride moderator may be maintained at the concentrations levels used during the initiating stage of the start-up process or gradually increased to the levels of target operating conditions. During the increase in temperature from the first temperature to the second temperature, the selectively value of the epoxidation reaction is held at the levels mentioned above during the initiating stage of the start-up process.

After achieving the second temperature, and in one embodiment of the present disclosure, the second temperature is maintained or held for a time period of about 10 hours to about 400 hours. In another embodiment, the second temperature is maintained or held for a time period of about 20 hours to about 300 hours. In yet another embodiment, the second temperature is maintained or held for a time period of about 40 hours to about 200 hours. During this maintaining or holding process at the second temperature, the levels of ethylene, oxygen and chloride moderator are maintained at the same levels as used during the initiating stage of the start-up process. During the maintaining or holding at the second temperature stage of the start-up process of the present disclosure, the selectively value of the epoxidation reaction is held at the levels mentioned above during the initiating stage of the start-up process.

In accordance with the present disclosure, the excess amount of chloride moderator used during the various stages of the start-up process of the present disclosure maintains the selectivity of the epoxidation reaction below that which is achieved utilizing conventional start-up processes. In particular, the chloride moderator level used during the various stages of the start-up process of the present disclosure maintains a selectivity value of the epoxidation below 86%. In prior art start-up processes, the various stages aim to increase the selectivity value of the epoxidation reaction.

It was unexpectedly determined that despite the low selectivity values achieved during the start-up process of the present disclosure, high selectivity catalysts that were subjected to the start-up process of the present disclosure exhibit increased performance, i.e., selectivity, activity and stability, during operation, as compared to equivalent high selectivity catalysts that were conditioned using a process in which a lower level of chloride moderator was used during the various stages of the start-up process.

After the conclusion of the maintaining or holding at the second temperature, the concentration of the chloride moderator is reduced from the level used in the previously described stages of the start-up process and the temperature of the conditioning process is reduced from the second temperature to a third temperature. The third temperature represents a normal starting temperature used in the industry for producing ethylene oxide. Typically, the third temperature is from about 180° C. to about 245° C. The reduced concentration of chloride moderator used at this stage of the process is typically within a range which is normally used during the early stages of production ethylene oxide. For example, the reduced level of chloride moderator used at this point of the present disclosure is from 0.5 ppm to 3 ppm.

After performing the above described start-up process, the activated Ag-based high selectivity catalyst can be used in the vapor phase production of ethylene oxide by conversion of ethylene to ethylene oxide in the presence of oxygen. Generally, the ethylene oxide production process is conducted by continuously contacting an oxygen-containing gas with ethylene in the presence of the catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. A typical process for the oxidation of ethylene to ethylene oxide comprises the vapor phase oxidation of ethylene with molecular oxygen in the presence of the catalyst of the present disclosure in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

The activated Ag-based high selectivity catalyst has been shown to be a particularly selective catalyst in the oxidation of ethylene with molecular oxygen to ethylene oxide. Selectivity values of at least about 83 mol % up to about 93 mol % are typically achieved. In some embodiments, the selectivity is from about 87 mol % to about 93 mole %. The conditions for carrying out such an oxidation reaction in the presence of the catalyst of the present disclosure broadly comprise those described in the prior art. This applies, for example, to suitable temperatures, pressures, residence times, diluent materials (e.g., nitrogen, carbon dioxide, steam, argon, and methane), the presence or absence of moderating agents to control the catalytic action (e.g., 1,2-dichloroethane, vinyl chloride or ethyl chloride), the desirability of employing recycle operations or applying successive conversion in different reactors to increase the yields of ethylene oxide, and any other special conditions which may be selected in processes for preparing ethylene oxide.

In the production of ethylene oxide, reactant feed mixtures typically contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or byproducts, unreacted materials are typically returned to the oxidation reactor. For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production (work rate) of 100-350 kg EO per cubic meters of catalyst per hour. More typically, the feed composition at the reactor inlet comprises 1-40% ethylene, 3-12% oxygen, 0.3-40% $CO_2$, 0-3% ethane, 0.3-20 ppmv total concentration of organic chloride moderator, and the balance of the feed comprised of argon, methane, nitrogen, or mixtures thereof.

Chloride moderators which can be employed in the present disclosure include, but are not limited to, organic halides such as $C_1$ to $C_8$ halohydrocarbons; such, as for example, methyl chloride, ethyl chloride, ethylene dichloride, vinyl chloride or mixtures thereof. Also suitable are hydrogen-free chlorine sources such as perhalogenated hydrocarbons and diatomic chlorine are particularly effective as moderators in gas phase epoxidation. Perhalogenated hydrocarbons refer to organic molecules in which all of the hydrogen atoms in a hydrocarbon have been substituted with halogen atoms; suitable examples are trichlorofluormethane and perchloroethylene. It is important that the concentration level of the moderator be controlled so as to balance a number of competing performance characteristics; for example, moderator concentration levels that result in improved activity may simultaneously lower selectivity. Controlling moderator concentration level is particularly important with the rhenium-containing catalysts of the present invention, because as the rhenium-containing catalysts age the moderator concentration must be carefully monitored so as to continually increase, within very small increments, because optimal selectivity values are obtained only within a narrow moderator concentration range.

A usual method for the ethylene epoxidation process comprises the vapor-phase oxidation of ethylene with molecular oxygen, in the presence of one of the aforementioned described catalysts, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long filled with catalyst. Such reactors include a reactor outlet which allows the olefin oxide, un-used reactants, and byproducts to exit the reactor chamber.

In other embodiments, the process of ethylene oxide production includes the addition of oxidizing gases to the feed to increase the efficiency of the process. For example, U.S. Pat. No. 5,112,795 discloses the addition of 5 ppm of nitric oxide to a gas feed having the following general composition: 8 volume % oxygen, 30 volume % ethylene, about 5 ppmw ethyl chloride, and the balance nitrogen.

The resulting ethylene oxide is separated and recovered from the reaction products using methods known in the art. The ethylene oxide process may include a gas recycle process wherein a portion or substantially all of the reactor effluent is readmitted to the reactor inlet after substantially removing the ethylene oxide product and byproducts. In the recycle mode, carbon dioxide concentrations in the gas inlet to the reactor may be, for example, from about 0.3 to about 6, preferably from about 0.3 to about 2.0, volume percent.

The following examples are provided to illustrate some aspects of the present disclosure, without limiting the scope of the present disclosure.

In each of the examples, a high selectivity catalyst (HSC) was used. The HSC used in each of the examples is now described in greater detail.

Stock Solution for HSC: 277.5 g of deionized water was placed in cooling bath to maintain temperature during the whole preparation under 50° C. At continuous stirring, 221.9 g of ethylenediamine (99+%, Aldrich) was added in small portions to avoid overheating. 174.1 g of oxalic acid dehydrate (ACS Certified Reagent, Fisher) was than added to the water-ethylenediamine solution in small portions. After all oxalic acid was dissolved, 326.5 g of high purity silver oxide (Ames Goldsmith Corp.) was added to solution in small portions. After all silver oxide was dissolved and the solution was cooled to about 35° C. it was removed from cooling bath. After filtration, the solution contained roughly 30 wt % silver, and had a specific gravity of 1.55 g/mL.

Carrier for HSC: For this catalyst, the carrier that was used was an conventional alpha alumina carrier whose surface area, water absorption and other properties fall within the ranges mentioned in the present disclosure.

Catalyst Preparation: A 150 g portion of the above mentioned carrier was placed in a flask and evacuated to about 0.1 torr prior to impregnation. To the above silver solution were added aqueous solutions of 17 wt. % of [Cs] as cesium hydroxide, 3.8 wt. % [Re] as ammonium perrhenate, 4 wt. % [Li] as $LiNO_3$, 4 wt. % [W] as ammonium metatugstate, and 5 wt. % [S] as ammonium sulfate in order to prepare a catalyst composition. After thorough mixing, the promoted silver solution was aspirated into the evacuated flask to cover the carrier while maintaining the pressure at about 0.1 torr. The vacuum was released after about 5 minutes to restore ambient pressure, hastening complete penetration of the solution into the pores. Subsequently, the excess impregnation solution was drained from the impregnated carrier.

Calcination of the wet catalyst was done on a moving belt calciner. In this unit, the wet catalyst was transported on a stainless steel belt through a multi-zone furnace. All zones of the furnace were continuously purged with pre-heated, ultra-high purity nitrogen and the temperature was increased gradually as the catalyst passes from one zone to the next. The heat was radiated from the furnace walls and from the pre-heated nitrogen. The wet catalyst entered the furnace at ambient temperature. The temperature in the catalyst layer was then increased gradually to a maximum of about 400° C. as the catalyst passed through the heated zones. In the last (cooling) zone, the temperature of the now activated HSC was immediately lowered to less than 100° C. before it emerged into ambient atmosphere. The total residence time in the furnace was approximately 45 minutes.

EXAMPLES

Example 1

In this example, a first HSC catalyst and a second HSC catalyst, both as described above, were conditioned using exactly the same conditioning process except that the first HSC catalyst was conditioned in 1 ppm ethyl chloride, and the second HSC catalyst was conditioned in 2 ppm ethyl chloride.

Notably, the following conditioning procedure was followed for each catalyst. After loading, the catalyst, nitrogen was passed through the reactor. Under the flow of nitrogen, the temperature of reactor was raised from ambient to 225° C. in 2-3 h. Upon reaching 225° C., the feed containing 8% $C_2H_4$, 4% $O_2$, 4% $CO_2$ and ethyl chloride (EC) at the target concentration in nitrogen ballast was introduced. As feed was introduced, the temperature started to raise with a ramp of 5° C./h to the target activation temperature. The catalyst was held at this temperature for a target duration time after which it was reduced to 230-235° C., chloride level was reduced to 1.5 ppm and feed was changed to operation feed. As the reaction took place, chloride was further optimized to achieve maximum selectivity at minimum temperature.

During the aforementioned conditioning procedure, the selectivity of the second HSC catalyst that was conditioned in 2 ppm ethyl chloride (EC) remained lower than the first HSC catalyst that was conditioned in 1 ppm EC. Moreover, and after completion of the conditioning process, the start of reaction selectivity (SOR) and the activity of the second HSC catalyst conditioned in 2 ppm EC were greater than the both the SOR and activity of the first HSC catalyst conditioned in 1 ppm EC. These results are evidenced in Tables 1 and 2.

TABLE 1

Selectivity Development During Start-Up: Conditioning
T = 255° C., duration 64 hrs, ethyl chloride,
EC = 1 ppm and 2 ppm in the feed: $C_2H_4/O_2/CO_2$ =
8 mol. %/4 mol. %/4 mol. %.

| | EC, Concentration | | | |
|---|---|---|---|---|
| | 1 ppm | | 2 ppm | |
| Condition, time | 0 hrs | 64 hrs | 0 hrs | 64 hrs |
| Selectivity | 74% | 86.7% | 75.5% | 82.5% |

TABLE 2

Start of Run Selectivity and Temperature After Start-Ups at EC = 1 ppm and 2 ppm. Feed: $C_2H_4/O_2/CO_2$ = 30 mol. %/7 mol. %/1 mol. %.

| EC, Concentration | Selectivity | Temperature |
|---|---|---|
| 1 ppm | 88.3% | 252.5° C. |
| 2 ppm | 89.4% | 247.5° C. |

Example 2

In this example, a first HSC catalyst and a second HSC catalyst, both as described above, were conditioned using exactly the same conditioning process except that the first HSC catalyst was conditioned in 1 ppm ethyl chloride, and the second HSC catalyst was conditioned in 4 ppm ethyl chloride.

Notably, the following condition procedure was followed for each catalyst. After loading, the catalyst nitrogen was passed through the reactor. Under the flow of nitrogen, the temperature of reactor was raised from ambient to 225° C. in 2-3 h. Upon reaching 225° C., the feed containing 8% $C_2H_4$, 4% $O_2$, 4% $CO_2$ and ethyl chloride (EC) at the target concentration in nitrogen ballast was introduced. As feed was introduced, the temperature started to raise with a ramp of 5° C./h to the target activation temperature. The catalyst was held at this temperature for a target duration time after which it is reduced to 230-235° C., chloride level was reduced to 1.5 ppm and feed was changed to operation feed. As the reaction took place, chloride was further optimized to achieve maximum selectivity at minimum temperature.

During the aforementioned conditioning procedure, the selectivity of the second HSC catalyst that was conditioned in 4 ppm ethyl chloride (EC) remained lower than the first HSC catalyst that was conditioned in 1 ppm EC. Moreover, and after completion of the conditioning process, the start of reaction selectivity (SOR) of the second HSC catalyst conditioned in 4 ppm EC was greater than the SOR of the first HSC catalyst conditioned in 1 ppm EC. These results are evidenced in Tables 3, 4 and 5.

TABLE 3

Selectivity Development During Start-Up. Conditioning T = 255° C., duration 15 hrs and 41 hrs, EC = 2 ppm and 4 ppm in feed: $C_2H_4/O_2/CO_2$ = 8 mol. %/4 mol. %/4 mol. %.

| | EC Concentration | | | |
|---|---|---|---|---|
| | 2 ppm | | 4 ppm | |
| Condition, time | 0 hrs | 15 hrs | 0 hrs | 41 hrs |
| Selectivity | 83.7% | 84.5% | 81.4% | 83.0% |

TABLE 4

Selectivity Records During Operation after Start-Ups in Table 3. Feed: $C_2H_4/O_2/CO_2$ = 25 mol. %/7 mol. %/2 mol. %.

| Conditioning | Reaction Time (hrs) | Selectivity (%) |
|---|---|---|
| T = 255° C., 15 hrs, 2 ppm | 150 hrs | 89% |
| | 300 hrs | 87.4% |
| | 600 hrs | 86.2% |
| | 800 hrs | 83.8% |
| T = 255° C., 41 hrs, 4 ppm | 150 hrs | 88.8% |
| | 300 hrs | 88.2% |
| | 600 hrs | 87.6% |
| | 800 hrs | 87.2% |

TABLE 5

Temperature Records During Operation after Start-Ups in Table 3. Feed: $C_2H_4/O_2/CO_2$ = 25 mol. %/7 mol. %/2 mol. %.

| Conditioning | Reaction Time (hrs) | Temperature (° C.) |
|---|---|---|
| T = 255° C., 15 hrs, 2 ppm | 150 hrs | 260° C. |
| | 300 hrs | 265.5° C. |
| | 600 hrs | 273° C. |
| | 800 hrs | 277.5° C. |
| T = 255° C., 41 hrs, 4 ppm | 150 hrs | 253° C. |
| | 300 hrs | 259° C. |
| | 600 hrs | 267° C. |
| | 800 hrs | 269.5° C. |

Example 3

In this example, a first HSC catalyst and a second HSC catalyst, both as described above, were conditioned using exactly the same conditioning process except that the first HSC catalyst was conditioned in 1 ppm ethyl chloride, and the second HSC catalyst was conditioned in 4 ppm ethyl chloride.

Notably, the following condition procedure was followed for each catalyst. After loading the catalyst, nitrogen was passed through the reactor. Under the flow of nitrogen, the temperature of reactor was raised from ambient to 225° C. in 2-3 h. Upon reaching 225° C., the feed containing 8% $C_2H_4$, 4% $O_2$, 4% $CO_2$ and ethyl chloride (EC) at the target concentration in nitrogen ballast was introduced. As feed was introduced, the temperature started to raise with a ramp of 5° C./h to the target activation temperature. The catalyst was held at this temperature for a target duration time after which it was reduced to 230-235° C., chloride level was reduced to 1.5 ppm and feed was changed to operation feed. As the reaction took place, chloride was further optimized to achieve maximum selectivity at minimum temperature.

During the aforementioned conditioning procedure, the selectivity of the second HSC catalyst that was conditioned in 4 ppm ethyl chloride (EC) remained lower than the first HSC catalyst that was conditioned in 1 ppm EC. Moreover, and after completion of the conditioning process, the start of reaction selectivity (SOR) of the second HSC catalyst conditioned in 4 ppm EC was greater than the SOR of the first HSC catalyst conditioned in 1 ppm EC. These results are evidenced in Tables 6, 7 and 8.

TABLE 6

Selectivity Development During Start-Up. Conditioning T = 245° C. and 255° C., duration 19 hrs and 64 hrs, EC = 1 ppm and 4 ppm in feed: $C_2H_4/O_2/CO_2$ = 8 mol. %/4 mol. %/4 mol. %.

| | T (° C.)/EC Concentration (ppm) | | | |
|---|---|---|---|---|
| | 245° C./1 ppm | | 255° C./4 ppm | |
| Condition, time | 0 hrs | 19 hrs | 0 hrs | 64 hrs |
| Selectivity | 77.5% | 88.2% | 82.0% | 82.5% |

TABLE 7

Selectivity Records During Operation after Start-Ups in Table 6. Feed: $C_2H_4/O_2/CO_2$ = 30 mol. %/7 mol. %/1 mol. %.

| Conditioning | Reaction Time (hrs) | Selectivity (%) |
|---|---|---|
| T = 245° C., | 200 hrs | 90.2% |
| 19 hrs, 1 ppm | 500 hrs | 90.0% |
| | 950 hrs | 90.1% |
| | 1900 hrs | 88.8% |
| | 2400 hrs | 88.0% |
| T = 255° C., | 200 hrs | 90.3% |
| 64 hrs, 4 ppm | 500 hrs | 90.0% |
| | 950 hrs | 90.1% |
| | 1900 hrs | 88.8% |
| | 2400 hrs | 88.0% |

TABLE 8

Temperature Records During Operation after Start-Ups in Table 3. Feed: $C_2H_4/O_2/CO_2$ = 30 mol. %/7 mol. %/1 mol. %.

| Conditioning | Reaction Time (hrs) | Temperature (° C.) |
|---|---|---|
| T = 245° C., | 200 hrs | 247.8° C. |
| 19 hrs, 1 ppm | 500 hrs | 250.5° C. |
| | 950 hrs | 252° C. |
| | 1900 hrs | 259.7° C. |
| | 2400 hrs | 263.7° C. |
| T = 255° C., | 200 hrs | 247.8° C. |
| 64 hrs, 4 ppm | 500 hrs | 246.7° C. |
| | 950 hrs | 248° C. |
| | 1900 hrs | 252.5° C. |
| | 2400 hrs | 254° C. |

While there have been shown and described what are presently believed to be the preferred embodiments of the present disclosure, those skilled in the art will realize that other and further embodiments can be made without departing from the spirit and scope of the present disclosure, and this disclosure includes all such modifications that are within the intended scope of the claims set forth herein.

What is claimed as new is:

1. A method for the start-up of a process for the epoxidation of ethylene comprising:
   initiating an epoxidation reaction by reacting a feed gas composition containing ethylene, oxygen and a chloride moderator in the presence of a silver-based epoxidation catalyst at a first temperature from about 180° C. to about 230° C., wherein said chloride moderator is present in the feed gas composition at a concentration of greater than 1 ppm, and wherein said epoxidation reaction has a selectivity of less than 86%;
   increasing the first temperature to a second temperature of about 235° C. to about 270° C. at a ramp of 0.5° C./h to about 10° C./h in the presence of the feed gas composition used during said initiating;
   maintaining the second temperature over a time period of from about 10 hours to about 400 hours in the presence of the feed gas composition used during said initiating;
   reducing the concentration of the chloride moderator in the feed gas composition below that used during said initiating; and
   reducing the second temperature to a third temperature in the presence of said feed gas composition including said reduced concentration of chloride moderator.

2. The method of claim 1, further comprising performing a treatment process prior to said initiating the epoxidation reaction, wherein said treatment process includes contacting the silver-based epoxidation catalyst with a gas stream containing said chloride moderator in a concentration of greater than 1 ppm.

3. The method of claim 1, wherein said concentration of said chloride moderator is greater than 2 ppm.

4. The method of claim 1, wherein said concentration of said chloride moderator is greater than 4 ppm.

5. The method of claim 1, wherein said selectivity value is less than 83%.

6. The method of claim 1, wherein said selectivity value is less than 80%.

7. The method of claim 1, wherein said second temperature is from about 240° C. to about 265° C.

8. The method of claim 1, wherein said second temperature is from about 245° C. to about 260° C.

9. The method of claim 1, wherein said time period of maintaining the second temperature is from about 20 hours to about 300 hours.

10. The method of claim 1, wherein said time period of maintaining the second temperature is from about 40 hours to about 200 hours.

11. The method of claim 1, wherein said chloride moderator is selected from the group consisting of $C_1$-$C_8$ halohydrocarbons.

12. The method of claim 1, wherein said chloride moderator is selected from the group consisting of methyl chloride, ethyl chloride, ethylene dichloride, and vinyl chloride.

13. The method of claim 1, wherein said chloride moderator is diatomic chlorine or a perhalogenated hydrocarbon.

14. The method of claim 1, wherein during the initiating step said ethylene is present in said feed gas composition in a concentration from about 3 volume % to about 30 volume %.

15. The method of claim 1, wherein during the initiating step said oxygen is present in said feed gas composition in a concentration from about 0.3 volume % to about 7 volume %.

16. The method of claim 1 wherein the method further comprises the addition of rhenium to the catalyst.

* * * * *